United States Patent [19]
Freedman et al.

[11] Patent Number: 5,182,387
[45] Date of Patent: Jan. 26, 1993

[54] BIS-DIBENZOAZEPINE COMPOUNDS

[75] Inventors: Jules Freedman, Cincinnati; Alan J. Bitonti, Maineville, both of Ohio

[73] Assignee: Merrell Dow Pharmaceuticals Inc., Cincinnati, Ohio

[21] Appl. No.: 784,496

[22] Filed: Oct. 30, 1991

[51] Int. Cl.$^5$ .............................................. C07D 223/24
[52] U.S. Cl. .................................... 540/590; 540/591; 540/592
[58] Field of Search ...................... 540/590, 591, 592; 514/217, 895

[56] References Cited

U.S. PATENT DOCUMENTS 3,196,155 7/1965 Gailliot et al. .................... 514/895

OTHER PUBLICATIONS

Kallmayer et al. Chemical Abstracts, vol. 96, 1982, Abstract 68789b.
Bitonti, A. J. et al., Science, vol. 242, pp. 1301–1303 (1988).
Bitonti, A. J. et al., The Lancet, pp. 1282–1283 (1989).
Kyle, D. E. et al., Transactions of the Royal Society of Tropical Medicine and Hygine 84, pp. 474–478 (1990).
Peters, W. et al., Annals of Tropical Medicine and Parasitology, vol. 84, No. 6, pp. 541–551 (1990).

Primary Examiner—Robert T. Bond
Assistant Examiner—E. C. Ward
Attorney, Agent, or Firm—Carolyn D. Moon

[57] ABSTRACT

Novel bis-dibenzoazepine compounds useful in the treatment of malaria and drug-resistant malaria.

15 Claims, No Drawings

BIS-DIBENZOAZEPINE COMPOUNDS

This invention generally relates to novel Bis-Dibenzoazepine compounds useful in the treatment of malaria.

BACKGROUND OF THE INVENTION

Maria remains a significant health threat to humans despite massive international attempts to eradicate the disease. Over 200 million people are said to have malaria and over one million deaths per year are associated with malaria in Africa alone.

Malaria is a disease of warm blooded animals caused by infection with a parasite of the genus Plasmodium. Four species, *P. vivax, P. falciparum, P. malariae*, and *P. ovale*, are known to infect humans. The parasite is transmitted to humans by the bite of Anopheles mosquitoes. Subsequent to mosquito bite, the parasite rapidly invades the blood cells of the victim. After an incubation period, generally lasting about 10 to 14 days, symptoms, consisting of chills, fever, headache, muscle pains, splenomegaly, and anemia, appear. This incubation period may be prolonged for many weeks and onset can be quite insidious. Red blood cells are at first altered and later destroyed by the infection. After an acute episode, the victim may be reinfected by the parasite which persists in the liver.

Drug therapy utilizing quinine, chloroquine, primaquine, and other agents has been the mainstay of therapy against malaria. However, drug-resistant strains of protozoa have developed and in some cases strains are resistant to many or all of the current therapeutic agents. In particular, *P. falciparum* malaria is quite prone to exhibit single and even multiple drug-resistance. While new agents are continually developed and introduced, resistance to such new agents also quickly develops. For example, mefloquine-resistant malaria was reported even before mefloquine licensure was completed. There is, thus, an urgent need for antimalarial agents which can be used in the treatment of drug-resistant malaria.

SUMMARY OF THE PRESENT INVENTION

The present invention comprises a bis-dibenzoazepine compound of formula 1:

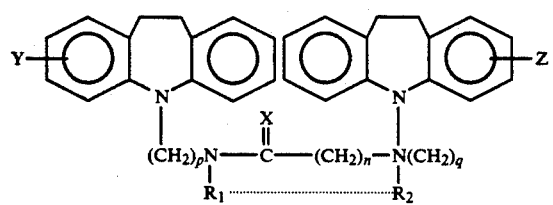

or a pharmaceutically acceptable salt thereof, wherein
X is O or $H_2$;
$R_1$ and $R_2$ are each independently H, $C_1$-$C_4$ alkyl, benzyl, or phenethyl, or, when there is a bond between $R_1$ and $R_2$ as represented by the dotted line, $R_1$ and $R_2$ taken together are ethylene;
Y and Z are each independently H, Cl, F, Br, $C_1$-$C_4$ alkyl, $C_1$-$C_4$ alkoxy, hydroxy or $CF_3$ moiety;
n is an integer of 1 to 10; and
p and q are each independently an integer of 2 to 4,
provided that when there is a bond between $R_1$ and $R_2$, X is $H_2$ and n is 1.

The present invention also comprises the use of the compound of formula 1 to prepare a pharmaceutical composition, and is useful in treating malarial infections.

DETAILED DESCRIPTION OF THE INVENTION

As used in the present invention, the term "$C_1$-$C_4$ alkyl" refers to a straight or branched alkyl such as methyl, ethyl, propyl, isopropyl, butyl, isobutyl, tert-butyl and the like. The term "$C_1$-$C_4$ alkoxy" refers to a straight or branched alkoxy such as methoxy, ethoxy, propoxy and the like. The term "Hal" or "halo" refers to chloro, bromo or iodo. The dotted line between $R_1$ and $R_2$ represents an optional double bond, i.e., $R_1$ and $R_2$ can each be unconnected separate moieties only attached to their respective nitrogen atoms or can together represent an ethylene group ($-CH_2CH_2-$) such that when X is $H_2$ and n is 1, a piperazine radical is formed as illustrated in compound (12) of Scheme D hereafter. When X is $H_2$, the carbon atom, to which X is attached is attached to two separate H atoms as well as adjacent nitrogen and carbon atoms. When p or q are each more than 2, it is intended that the alkylene moiety formed thereby forms a straight chain, the terminal ends of which attach to nitrogen atoms.

The bis-dibenzoazepine compounds of the formula 1 can form pharmaceutically acceptable salts with any non-toxic, organic or inorganic acid. Illustrative inorganic acids which form suitable salts include hydrochloric, hydrobromic, sulphuric and phosphoric acid and acid metals salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methanesulfonic, trifluoromethanesulfonic and 2-hydroxyethane sulfonic acid.

The compounds of formula 1 wherein $R_1$ and $R_2$ are each independently $C_1$-$C_4$ alkyl, benzyl or phenethyl can be prepared by techniques and procedures well known and appreciated by one of ordinary skill in the art. The choice of any specific route of preparation is dependent upon a variety of factors. The following schemes are examples of general synthetic procedures for preparing these compounds. In Scheme A, all substituents are as previously defined unless otherwise indicated.

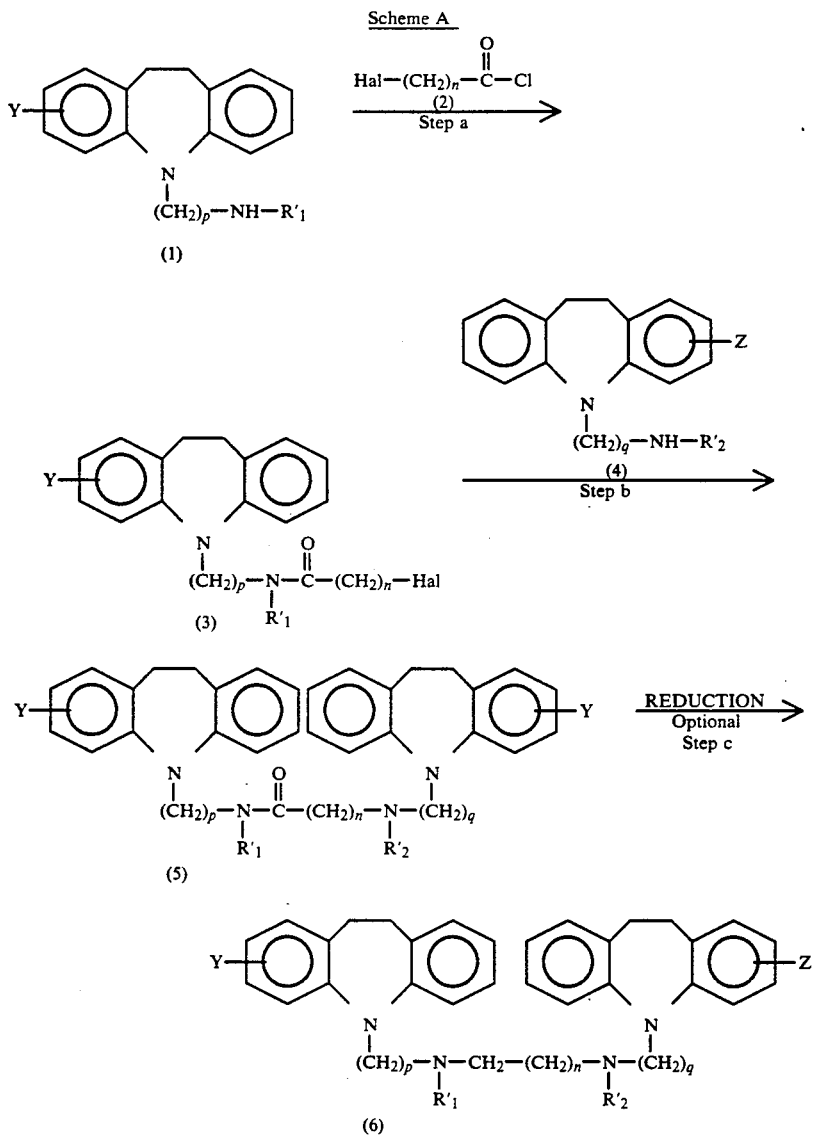

R′₁ and R′₂ = C₁-C₄ alkyl, benzyl or phenethyl

Scheme A provides a general synthetic procedure for preparing the compounds of formula 1 wherein R₁ and R₂ are each independently C₁-C₄ alkyl, benzyl or phenethyl.

In step a, the appropriate 5-(alkylaminoalkyl)-10,11-dihydro-5H-dibenzo[b,f]azepines of structure (1) is amidated with the appropriate halo-alkanoyl chloride of structure (2) to give the corresponding 5-([(halo-acylalkyl)alkylamino]alkyl)-10,11-dihydro-5H-dibenzo[b,f]azepine of structure (3).

For example, the appropriate 5-(alkylaminoalkyl)-10,11-dihydro-5H-dibenzo[b,f]azepines of structure (1) is contacted with a molar equivalent of a base such as triethylamine and a molar equivalent of an appropriate halo-alkanoyl chloride of structure (2). The reactants are typically contacted in a suitable organic solvent such as dichloromethane. The reactants are typically stirred together for a period of time ranging from 10-24 hours and at a temperature range of from 0° C. to room temperature. The 5-([(halo-acyl-alkyl)alkylamino]alkyl)-10,11-dihydro-5H-dibenzo[b,f]azepine of structure (3) is recovered from the reaction zone by extractive methods as is known in the art. It may be purified by chromatography.

In step b, the halo functionality of the appropriate 5-([(halo-acyl-alkyl)alkylamino]alkyl)-10,11-dihydro-5H-dibenzo[b,f]azepine of structure (3) is displaced with the appropriate 5-(alkylaminoalkyl)-10,11-dihydro-5H-dibenzo[b,f]azepines of structure (4) to give the corresponding N,N′-bis[3-(10,11-dihydro-5H-dibenzo[b,f]azepino)alkyl]-N,N′-dialkylalkanoamide of structure (5).

For example, the appropriate 5-([(halo-acylalkyl)alkylamino]alkyl)-10,11-dihydro-5H-dibenzo[b,f]azepine of structure (3) is contacted with a molar equivalent of the appropriate 5-(alkylaminoalkyl)-10,11-dihydro-5H-dibenzo[b,f]azepines of structure (4) and a molar equivalent of an appropriate base such as potassium carbonate. The reactants are typically contacted in a suitable organic solvent such as acetonitrile. The reactants are typically stirred together for a period of time ranging from 2-12 hours at a temperature range of from room temperature to reflux. The N,N'-bis[3-(10,11-dihydro-5H-dibenzo[b,f]azepino)alkyl]-N,N'-dialkylalkanoamide of structure (5) is recovered from the reaction zone by evaporation of the solvent. It may be purified by chromatography and converted to a suitable acid-addition salt.

In optional step c, the appropriate N,N'-bis[3-(10,11-dihydro-5H-dibenzo[b,f]azepino)alkyl]-N,N'-dialkylalkanoamide of structure (5) is reduced to give the corresponding N,N'-bis[(10,11-dihydro-5H-dibenzo[b,f]azepino)alkyl]-N,N'-dialkylalkanediamine of structure (6).

For example, the appropriate N,N'-bis[3-(10,11-dihydro-5H-dibenzo[b,f]azepino)alkyl]-N,N'-dialkylalkanoamide of structure (5) is contacted with 2 molar equivalents of lithium aluminum hydride. The reactants are typically contacted in a suitable organic solvent such as ethyl ether. The reactants are typically stirred together for a period of time ranging from 10 minutes to 5 hours and at a temperature range of from 0° C. to reflux. The N,N'-bis[(10,11-dihydro-5H-dibenzo[b,f]azepino)alkyl]-N,N'-dialkylalkanediamine of structure (6) is recovered from the reaction zone by extractive methods as is known in the art. It may be purified by chromatography and converted to its acid-addition salt.

Starting materials for use in Scheme A are readily available to one of ordinary skill in the art. For example, certain 5-(alkylaminoalkyl)-10,11-dihydro-5H-dibenzo[b,f]azepines of structures (1) and (4) are described in Swiss Patent Application of Walter Schindler, Charles Gansser and Henri Dietrich, # 377,824, Jul. 15, 1964 and in *Intern. J. Neuropharmacol*, 3(6), 611-21 1964.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

N,N'-Bis[3-(10,11-dihydro-5H-dibenzo[b,f]azepino)-propyl]-N,N'-dimethylacetamide Oxalate—MDL 102,256

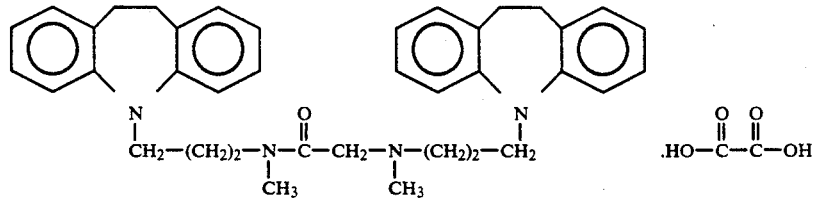

Step a:
5-(3-[(2-chloro-1-oxo-ethyl)methylamino]propyl)-10,11-dihydro-5H-dibenzo[b,f]azepine Dissolve 5-(3-methylaminopropyl)-10,11-dihydro-5H-dibenzo[b,f]azepine (7.0 g, 0.026 mol) and triethylamine (4 mL) in dichloromethane (100 mL) and cool with an ice-bath. Add, by dropwise addition, a solution of chloroacetyl chloride (3.23 g, 0.0286 mol) in dichloromethane (25 mL). Stir at room temperature for 12 hours, shake with dilute hydrochloric acid and dry (MgSO$_4$). Evaporate the solvent in vacuo to give the title compound as an oil.

Step b:
N,N'-Bis[3-(10,11-dihydro-5H-dibenzo[b,f]azepino)-propyl]-N,N'-dimethylacetamide Oxalate Mix 5-(3-[(2-chloro-1-oxo-ethyl)methylamino]-propyl)-10,11-dihydro-5H-dibenzo[b,f]azepine (3.5 g, 0.01 mol), 5-(3-methylaminopropyl)-10,11-dihydro-5H-dibenzo[b,f]azepine (2.7 g, 0.01 mol) potassium carbonate (1.5 g) and acetonitrile (100 mL). Stir at reflux temperature for 4 hours, filter and evaporate the solvent in vacuo. Purify by silica gel chromatography and convert to the oxalate salt to give the title compound (5.0 g); mp 165°-167° C.

Anal. Calcd for C$_{38}$H$_{44}$N$_4$O.C$_2$H$_2$O$_4$: C, 72.48; H, 7.00; N, 8.45; Found: C, 72.37; H, 7.07; N, 8.49.

EXAMPLE 2

N,N'-Bis[3-(10,11-dihydro-5H-dibenzo[b,f]azepino)-propyl]-N,N'-dimethylethanediamine Maleate—MDL 102,837

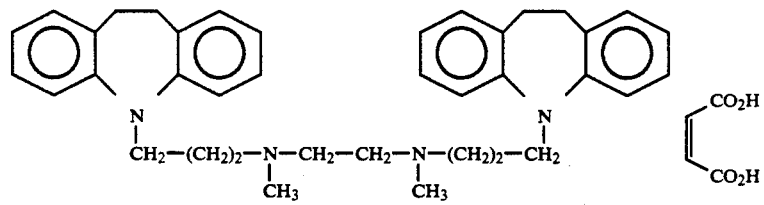

Dissolve N,N'-bis[3-(10,11-dihydro-5H-dibenzo[b,f]azepino)propyl]-N,N'-dimethylacetamide (3.64 g, 0.006 mol) in ethyl ether (50 mL). Add, by dropwise addition, to an ice-cooled suspension of lithium aluminum hydride (0.5 g) in ethyl ether (50 mL). Stir at reflux temperature for 0.5 hours, cool in ice and carefully decompose excess lithium aluminum hydride with water (1.2 mL). Filter and treat the filtrate with a solution of maleic acid in ethyl ether. Collect the resulting precipitate and recrystallize (methanol/acetonitrile) to give the title compound (3.01 g); mp 168°-170° C.

Anal. Calcd for $C_{38}H_{46}N_4.1.5C_4H_4O_4$: C, 72.12; H, 7.15; N, 7.65; Found: C, 72.34; H, 7.22; N, 7.84.

Examples 3-6 are prepared according to procedures described in Examples 1-2 above.

EXAMPLE 3

N,N'-Bis[3-(10,11-dihydro-5H-dibenzo[b,f]azepino)-propyl]-N,N'-dimethylpropanediamine Maleate—MDL 100,639

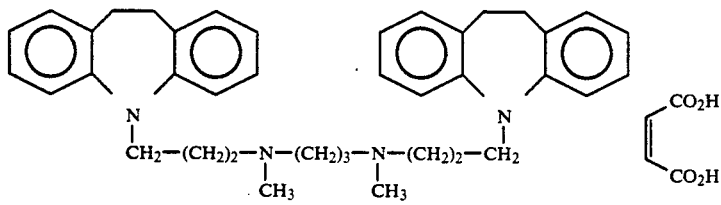

mp 200°-202° C.
Anal. Calcd for $C_{39}H_{48}N_4.2C_4H_4O_4$: C, 70.12: H, 7.01; N, 6.96; Found: C, 70.19; H, 7.08; N, 6.90.

EXAMPLE 4

N,N'-Bis[3-(10,11-dihydro-5H-dibenzo[b,f]azepino)-propyl]-N,N'-dimethylbutanediamine Fumarate—MDL 102,651

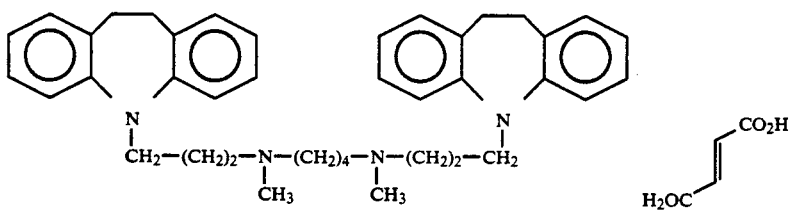

mp 211°-213° C.
Anal. Calcd for $C_{40}H_{50}N_4.2C_4H_4O_4$: C, 70.39; H, 7.14; N, 6.84; Found C, 70.19: H, 7.33; N, 6.84.

EXAMPLE 5

N,N'-Bis[3-(10,11-dihydro-5H-dibenzo[b,f]azepino)-propyl]-N,N'-dimethylpentanediamine Maleate—MDL 100,747

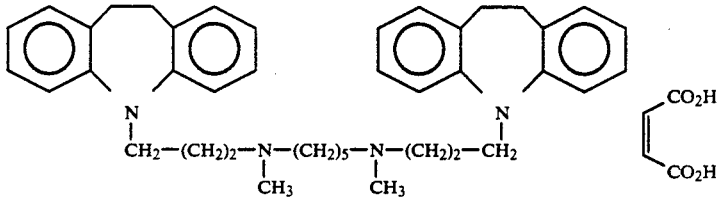

mp 118°-120° C.
Anal. Calcd for $C_{41}H_{52}N_4.2C_4H_4O_4.H_2O$: C, 69.15; H, 7.34; N, 6.58; Found: C, 69.30; H, 7.59; N, 6.54.

EXAMPLE 6

N,N'-Bis[3-(10,11-dihydro-5H-dibenzo[b,f]azepino)-propyl]-N,N'-dimethylhexanediamine Fumarate—MDL 100,987 mp 196°-197° C.
Anal. Calcd for $C_{42}H_{54}N_4.2C_4H_4O_4$: C, 70.89; H, 7.38; N, 6.62; Found: C, 70.71; H, 7.61; N, 6.56.

The compounds of formula 1 wherein $R_1$ and $R_2$ are equivalent and selected from the group consisting of $C_1$-$C_4$ alkyl, benzyl or phenethyl, Y and Z are equivalent, p and q are equivalent and X is $H_2$ can be prepared by techniques and procedures well known and appreciated by one of ordinary skill in the art. General synthetic procedures for preparing these compounds is set forth in Scheme B. In Scheme B, all substituents are as previously defined unless otherwise indicated.

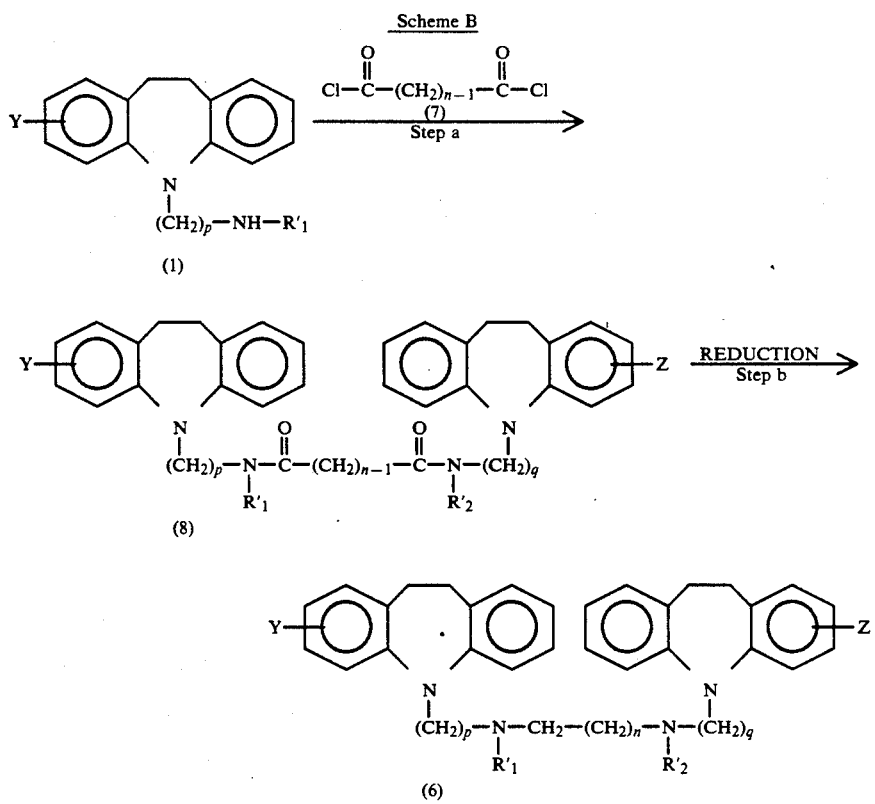

Scheme B

R'₁ = R'₂ = C₁-C₄ alkyl, benzyl or phenethyl
Y = Z
p = q

Scheme B provides general synthetic procedure for preparing compounds of formula 1 wherein $R_1$ and $R_2$ are equivalent and selected from the group consisting of $C_1$-$C_4$ alkyl, benzyl or phenethyl, Y and Z are equivalent, p and q are equivalent and X is $H_2$.

In step a, the appropriate 5-(alkylaminoalkyl)-10,11-dihydro-5H-dibenzo[b,f]azepines of structure (1) is bis-amidated with the appropriate dialkanoyl chloride of structure (7) to give the corresponding N,N'-bis[(10,11-dihydro-5H-dibenzo[b,f]azepino)alkyl]-N,N'-dialkyl-dicarboxamide of structure (8).

For example, the appropriate 5-(alkylaminoalkyl)-10,11-dihydro-5H-dibenzo[b,f]azepines of structure (1) is contacted with a molar equivalent of an appropriate base such as triethylamine and 0.5 molar equivalents of an appropriate dialkanoyl chloride of structure (7). The reactants are typically contacted in a suitable organic solvent such as dichloromethane. The reactants are typically stirred together for a period of time ranging from 10 minutes to 5 hours and at a temperature range of from 0° C. to room temperature. The N,N'-bis[(10,11-dihydro-5H-dibenzo[b,f]azepino)alkyl]-N,N'-dialkyl-dicarboxamide of structure (8) is recovered from the reaction zone by extractive methods as is known in the art. It may be purified by chromatography.

In step b, the appropriate N,N'-bis[(10,11-dihydro-5H-dibenzo[b,f]azepino)alkyl]-N,N'-dialkyl-dicarboxamide of structure (8) reduced to give the corresponding N,N'-bis[(10,11-dihydro-5H-dibenzo[b,f]azepino)alkyl]-N,N'-dialkylalkanediamine of structure (6) as described previously in Scheme A, optional step c.

Starting materials for use in Scheme B are readily available to one of ordinary skill in the art.

The following example presents a typical synthesis as described in Scheme B. This example is understood to be illustrative only and is not intended to limit the scope of the present invention in any way.

EXAMPLE 7

N,N'-Bis[3-(10,11-dihydro-5H-dibenzo[b,f]azepino)-propyl]-N,N'-dibenzylbutanediamine—MDL#101,648

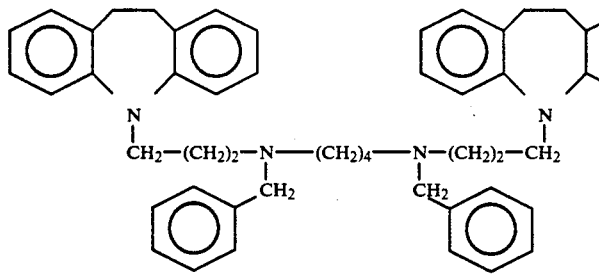

Step a:
N,N'-Bis[3-(10,11-dihydro-5H-dibenzo[b,f]azepino)-propyl]-N,N'-dibenzyl-succinamide Dissolve 5-(3-benzylaminopropyl)-10,11-dihydro-5H-dibenzo[b,f]azepine (3.71 g, 0.01 mol) and triethylamine (1.5 mL) in dichloromethane (25 mL) and cool in an ice bath. Add, by dropwise addition, a solution of succinoyl chloride (0.84 g, 0.005 mol) in dichloromethane (25 mL). Stir for 0.5 hours, shake with dilute hydrochloric acid followed by water. Dry (MgSO4), filter and evaporate the solvent in vacuo to give the title compound as an oil.

Step b:
N,N'-Bis[3-(10,11-dihydro-5H-dibenzo[b,f]azepino)-propyl]-N,N'-dibenzylbutanediamine Dissolve N,N'-Bis[3-(10,11-dihydro-5H-dibenzo[b,-f]azepino)propyl]-N,N'-dibenzyl-succinamide (0.01 mol) in ethyl ether (25 mL). Add, by dropwise addition, to a suspension of lithium aluminum hydride (1.1 g) in ethyl ether (100 mL). Stir at reflux temperature for 1 hour, cool in an ice bath and carefully decompose excess lithium aluminum hydride with 10% sodium hydroxide (4 mL). Filter and evaporate the solvent in vacuo to give a solid residue. Purify by recrystallization (ethyl acetate) to give the title compound; mp 145°–147° C.

Anal. Calcd for $C_{52}H_{58}N_4$: C, 84.51; H, 7.91; N, 7.58; Found: C, 84.36; H, 8.04; N, 7.59.

The compounds of formula 1 wherein $R_1$ and $R_2$ are each H can be prepared by techniques and procedures well known and appreciated by one of ordinary skill in the art. General synthetic procedures for preparing these compounds is set forth in Scheme C. In Scheme C, all substituents are as previously defined unless otherwise indicated.

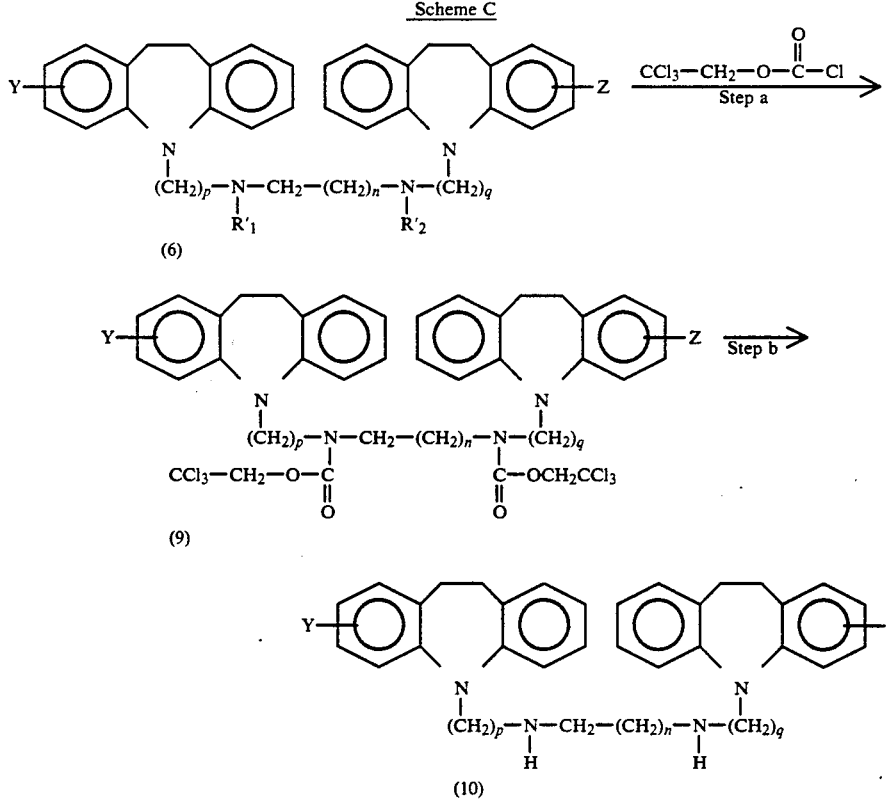

Scheme C

Scheme C

R'₁ and R'₂ are H

Scheme C provides general synthetic procedures for preparing the compounds of formula 1 wherein R₁ and R₂ are each H.

In step a, the N,N-dialkyl functionalities of the appropriate N,N'-bis[(10,11-dihydro-5H-dibenzo[b,f]azepino)alkyl]-N,N'-dialkylalkanediamine of structure (6) are removed and the 2,2,2-trichloroethylcarbamates formed to give the corresponding N,N'-bis[(10,11-dihydro-5H-dibenzo[b,f]azepino)alkyl]-N,N'-dicarboxyalkanediamine, bis(2,2,2-trichloroethyl)ester of structure (9).

For example, the appropriate N,N'-bis[(10,11-dihydro-5H-dibenzo[b,f]azepino)alkyl]-N,N'-dialkylalkanediamine of structure (6) is contacted with 2 molar equivalents of a suitable base such as potassium carbonate and 2 molar equivalents of 2,2,2-trichloroethyl chloroformate. The reactants are typically contacted in a suitable organic solvent such as benzene. The reactants are typically stirred together at room temperature for a period of time ranging from 5-24 hours. The N,N'-bis[(10,11-dihydro-5H-dibenzo[b,f]azepino)alkyl]-N,N'-dicarboxyalkanediamine, bis(2,2,2-trichloroethyl)ester of structure (9) is recovered from the reaction zone by extractive methods as is known in the art. It may be purified by chromatography.

In step b, the bis(2,2,2-trichloroethyl)ester functionality of the appropriate N,N'-bis[(10,11-dihydro-5H-dibenzo[b,f]azepino)alkyl]-N,N'-dicarboxyalkanediamine, bis(2,2,2-trichloroethyl)ester of structure (9) is removed to give the corresponding N,N'-bis[(10,11-dihydro-5H-dibenzo[b,f]azepino)alkyl]alkanediamine of structure (10).

For example, the appropriate N,N'-bis[(10,11-dihydro-5H-dibenzo[b,f]azepino)alkyl]-N,N'-dicarboxyalkanediamine, bis(2,2,2-trichloroethyl)ester of structure (9) is contacted with a molar excess of zinc dust. The reactants are typically contacted in a suitable acidic solvent such as acetic acid. The reactants are typically stirred together at room temperature for a period of time ranging from 5-24 hours. The N,N'-bis[(10,11-dihydro-5H-dibenzo[b,f]azepino)alkyl]alkanediamine of structure (10) is recovered from the reaction zone by extractive methods as is known in the art. It may be purified by chromatography and converted to its acid-addition salt.

Starting materials for use in Scheme C are readily available to one of ordinary skill in the art.

The following example presents a typical synthesis as described in Scheme C. This example is understood to be illustrative only and is not intended to limit the scope of the present invention in any way.

EXAMPLE 8
N,N'-Bis[3-(10,11-dihydro-5H-dibenzo[b,f]azepino)propyl]butanediamine Maleate—MDL 102,547

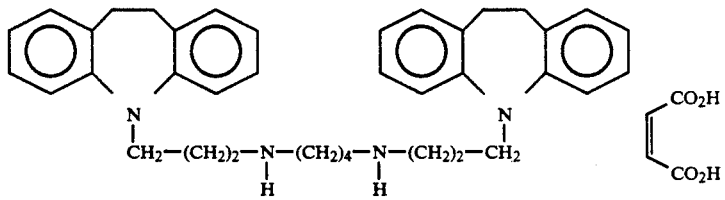

Step a:
N,N'-Bis[3-(10,11-dihydro-5H-dibenzo[b,f]azepino)propyl]-N,N'-dicarboxybutanediamine, bis(2,2,2-trichloroethyl)ester Suspend N,N'-bis[3-(10,11-dihydro-5H-dibenzo[b,f]azepino)propyl]-N,N'-dibenzylbutanediamine (2.63 g, 0.0035 mol) and potassium carbonate (1.0 g) in benzene (75 mL). Add, by dropwise addition, a solution of trichloroethyl chloroformate (2.26 g, 0.01 mol) in benzene (25 mL). Stir at room temperature for 18 hours, wash with dilute hydrochloric acid, water, dilute sodium hydroxide and saturated sodium chloride. Dry (MgSO₄), evaporate the solvent in vacuo and purify by silia gel chromatography followed by recrystallization (cyclohexane) to give the title compound (2.20 g); mp 145°-147° C.

Anal. Calcd for $C_{44}H_{48}Cl_6N_4O_4$: C, 58.10; H, 5.32; N, 6.16; Found: C, 58.25; H, 5.33; N, 6.34.

Step b:
N,N'-Bis[3-(10,11-dihydro-5H-dibenzo[b,f]azepino)propyl]butanediamine Maleate Suspend N,N'-bis[3-(10,11-dihydro-5H-dibenzo[b,f]azepino)propyl]-N,N'-dicarboxybutanediamine, bis(2,2,2-trichloroethyl)ester (2.00 g) in 95% acetic acid (60 mL). Treat with zinc dust (10 g) in two portions over 0.5 hours. Stir the mixture at room temperature for 18 hours and filter. Evaporate the solvent in vacuo, take up the residue in chloroform and wash with dilute sodium hydroxide. Evaporate the solvent in vacuo, dissolve in a minimum amount of acetone and treat with an ethyl ether solution of maleic acid. Collect the precipitate by filtration and recrystallize (acetonitrile) to give the title comound (1.21 g); mp 193°-194° C.

Anal. Calcd for $C_{38}H_{46}N_4 \cdot 2C_4H_4O_4$: C, 69.85; H, 6.88; N, 7.08; Found: C, 69.88; H, 7.05; N, 7.00.

The compounds of formula 1 wherein R₁ and R₂ together are ethylene can be prepared by techniques and procedures well known and appreciated by one of ordinary skill in the art. General synthetic procedures for preparing these compounds is set forth in Scheme D. In Scheme D, all substituents are as previously defined unless otherwise indicated.

Scheme D

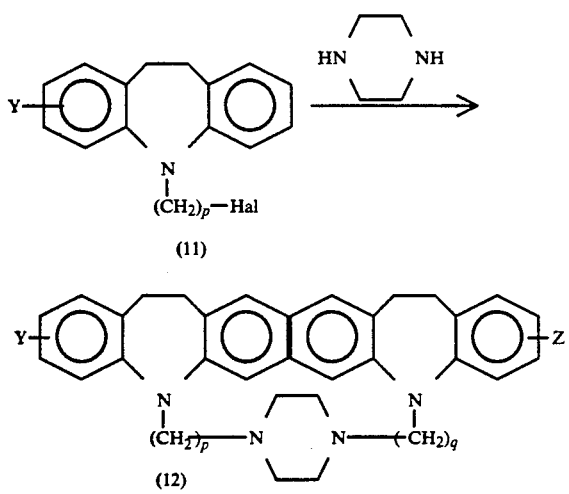

Scheme D provides general synthetic procedure for preparing the compounds of formula 1 wherein $R_1$ and $R_2$ together are ethylene, X is $H_2$ and n is 1.

In step a, the appropriate 5-(haloalkyl)-10,11-dihydro-5H-dibenzo[b,f]azepine of structure (11) is displaced with piperazine to give the corresponding 1,4-bis[(10,11-dihydro-5H-dibenzo[b,f]azepino)alkyl]piperazine of structure (12).

For example, the appropriate 5-(haloalkyl)-10,11-dihydro-5H-dibenzo[b,f]azepine of structure (11) is contacted with 0.5 molar equivalents of piperazine and a molar excess of potassium iodide. The reactants are typically contacted in a suitable organic solvent such as 2-butanone. The reactants are typically stirred together at reflux temperature for a period of time ranging from 5–55 hours. The 1,4-bis[(10,11-dihydro-5H-dibenzo[b,-f]azepino)alkyl]piperazine of structure (12) is recovered from the reaction zone by evaporation of the solvent. It may be purified by chromatography and converted to its acid-addition salt.

Starting materials for use in Scheme D are readily available to one of ordinary skill in the art. For example, 5-(haloalkyl)-10,11-dihydro-5H-dibenzo[b,f]azepines of structure (11) are described in U.S. Pat. No. 3,123,610 issued to J. W. Cusic on Mar. 3, 1964.

The following example presents a typical synthesis as described in Scheme D. This example is understood to be illustrative only and is not intended to limit the scope of the present invention in any way.

EXAMPLE 9

1,4-Bis[3-(10,11-dihydro-5H-dibenzo[b,f]azepino)-propyl]piperazine Maleate—MDL 100,653

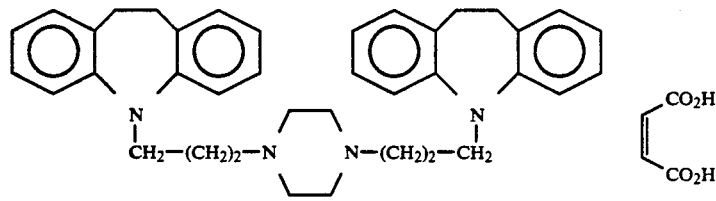

Reflux a mixture of piperazine (0.86 g, 0.01 mol), 5-(3-chloropropyl)-10,11-dihydro-5H-dibenzo[b,f]azepine (6.0 g), potassium iodide (3.0 g) and 2-butanone (50 mL) for 48 hours. Cool, filter and evaporate the solvent in vacuo. Triturate with water and stir the insoluble solids with a solution of maleic acid in ethyl ether for 18 hours. Filter the precipitate and recrystallize (methanol) to give the title compound (5.8 g); mp 213°–215° C.

Anal. Calcd for $C_{38}H_{44}N_4 \cdot 2C_4H_4O_4$: C, 70.03; H, 6.64; N, 7.10; Found: C, 69.84; H, 6.42; N, 7.10.

The term "drug-resistant malaria" means a malarial infection, particularly of malaria resulting from infection by P. falciparum in humans, which is substantially not responsive to treatment with existing therapeutic agents such as quinine, chloroquine, amodiaquine, primaquine, or mefloquine. "Patient" as used herein is any warm blooded mammal capable of being infected with malaria, including humans.

Therapeutic and prophylactic agents used in treating and preventing malarial infections of warm blooded animals and those antimalarial agents used in the combination therapy of this invention include any therapeutic agent used in treating or preventing non-drug-resistant malarial infections and those therapeutic and prophylactic agents currently used in treating and preventing drug-resistant malarial infections such as mefloquine. As used herein, the term "antimalarial agent" specifically does not include the compounds of formula 1. Some examples of antimalarial agents used in treating and preventing malarial infections are various quinoline derivatives such as quinine, chloroquine, primaquine, sulfadoxine, mefloquine, and pyrimethamine. Various salts of these agents may also be employed and combinations of these various agents are routinely utilized.

The term "conjunctive therapy" as used herein contemplates the administration of a formula 1 compound immediately prior to, concomitantly with, or subsequent to treatment with the antimalarial agent or agents whether to treat or prevent such an infection. The compounds of formula 1 can be made available in separate dosage forms or combined with antimalarial agents.

Typically, treatment of a patient infected with a drug-resistant malaria, requires doses of the antimalarial agent or agents many times the normal dosage, and such therapy is heroic in nature, i.e., in an effert to save the life of the patient, doses of antimalarial agents normally regarded as "overdosages" are used. While the conjunctive therapy of this invention could, in some cases, provide for dosages of less antimalarial agent than would be possible in the absence of the formula 1 compound, the dose of antimalarial agent employed in the method of this invention can be essentially that dose which would be employed in the absence of the formula 1 compound when used to treat a non drug-resistant protozoal infection. The dosages for antimalarial agents are well known to one skilled in the art.

A therapeutically or prophylactically effective amount of a compound of formula 1 varies from about 0.1 milligrams per kilogram of body weight per day (mg/kg/day) to about 100 mg/kg/day. Preferred amounts are expected to vary from about 1 to about 10 mg/kg/day.

The preferred route of administration is oral administration. For oral administration the compounds can be formulated into solid or liquid preparations such as capsules, pills, tablets, troches, lozenges, melts, powders, solutions, suspensions, or emulsions.

The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate.

Suitable soaps for inclusion in the parenteral formulations include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Pharmaceutical compositions of the antimalarial agents such as chloroquine are widely available and can be used in the practice of this invention. Dosage forms of the formula (1) compounds of this invention may contain from 5 to 250 mg and can be administered to a patient from 1 to 3 or 4 times daily, as required.

As shown by Table 1, the compounds of the present invention have antimalarial activity on their own without other antimalarial agents. This antimalarial activity can be tested using a number of methods. For example, the compounds of formula 1 listed in Table 1 were tested for antimalarial activity against chloroquine-sensitive strain of Plasmodium falciparum (clone D6).

TABLE 1

| COMPOUND | $IC_{50}$, ng/ml CLONE D6 |
| --- | --- |
| chloroquine | 7 |
| desipramine (9384) | 15000 |
| 100,987DV - Example #6 | 210 |
| 102,547DG - Example #8 | 48 |
| 102,651DV - Example #4 | 240 |

The methods for the growth of the malaria parasite, the testing of drugs for antimalarial effects and the clone are described in Science 242, 1301-1303 1988. Chloroquine is an antimalarial agent and desipramine is an agent shown to have utility in reversing chloroquine resistance in the malaria parasite of Plasmodium falciparum as described in the aforementioned Science article.

The compounds of formula 1 also reverse drug-resistant malarial when a reversal of drug-resistant malarial amount of the compounds of formula 1 are administered to the patient, preferably with an effective amount of an antimalarial agent (conjunctive therapy). Generally, "treatment" of malaria, as used herein, includes not only the administration of the compounds of the present invention to patients already infected with malaria, but also the administration of the compounds of the present invention to patients not infected with malaria, i.e., prophylactic treatment.

Referring to Table 2, the antimalarial activity of compounds of formula 1 were tested using the multidrug resistant Plasmodium falciparum clone W-2. The methods for the growth of the malaria parasite, the testing of drugs for antimalarial effects and the clone are described in Science 242, 1301-1303 1988.

As the data shows in Table 2, the compounds of the present invention are effective against drug-resistant *Plasmodium falciparum*. The right column shows the concentration of the compound in ng/ml required to achieve 50% reversal of the chloroquine resistance in clone W-2.

TABLE 2

| COMPOUND | $IC_{50}$, ng/ml CLONE W-2 | Conc. in ng/ml for 50% Reversal of chloroquine |
|---|---|---|
| chloroquine | 160 | |
| desipramine (9384) | 300 | 35 |
| 100,639AF - example 3 | 385 | 72 |
| 100,653DG - example 9 | >5000 | >200 |
| 100,747DG - example 5 | 180 | 56 |
| 100,987DV - example 6 | 140 | 52 |
| 102,256P - example 1 | 3574 | >200 |
| 102,547DB - example 8 | 110 | 105 |
| 102,651DV - example 4 | 56 | 14 |
| 102,837GH - example 2 | 1507 | >200 |

Some compounds of formula 1 have also been shown to have a synergistic effect with antimalarial agents. Compound MDL 102,651, exemplified in Example 4, has a synergistic effect with chloroquine against chloroquine-resistant *Plasmodium falciparum*. Isobologram analysis was carried out according to the method of Martin, et al., (1987) *Science* 235, 899–901 and Berenbaum, (1978) *Journal of Infectious Diseases* 137, 122–130 (data not shown).

Compounds of formula 1 wherein p and q are each 3 are preferred. Also preferred are compounds where each of $R_1$ and $R_2$ are methyl. X is preferably $H_2$, and n is preferably 1-5.

What is claimed is:

1. A compound of the formula:

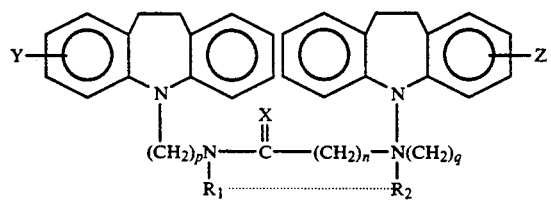

or a pharmaceutically acceptable salt thereof, wherein

X is O or $H_2$;

$R_1$ and $R_2$ are each independently H, $C_1$-$C_4$ alkyl, benzyl, or phenethyl, or, when there is a bond between $R_1$ and $R_2$ as represented by the dotted line, $R_1$ and $R_2$ taken together are ethylene;

Y and Z are each independently H, Cl, F, Br, $C_1$-$C_4$ alkyl, $C_1$-$C_4$ alkoxy, hydroxy or $CF_3$ moiety;

n is an integer of 1 to 10; and p and q are each independently an integer of 2 to 4, provided that when there is a bond between $R_1$ and $R_2$, X is $H_2$ and n is 1.

2. The compound of claim 1 in which p and q are each 3.

3. The compound of claim 1 in which n is between 1 and 5.

4. The compound of claim 1 in which Y and Z are each H.

5. The compound of claim 1 in which $R_1$ and $R_2$ are each methyl.

6. The compound of claim 1 in which p and q are each 3, n is between 1 and 5, and Y and Z are each H.

7. A compound of claim 1 which is N,N'-Bis[3-(10,11-dihydro-5H-dibenzo[b,f]azepino)propyl]-N,N'-dimethylacetamide Oxalate.

8. A compound of claim 1 which is N,N'-Bis[3-(10,11-dihydro-5H-dibenzo[b,f]azepino)propyl]-N,N'-dimethylethanediamine Maleate.

9. A compound of claim 1 which is N,N'-Bis[3-(10,11-dihydro-5H-dibenzo[b,f]azepino)propyl]-N,N'-dimethylpropanediamine Maleate.

10. A compound of claim 1 which is N,N'-Bis[3-(10,11-dihydro-5H-dibenzo[b,f]azepino)propyl]-N,N'-dimethylbutanediamine Fumarate.

11. A compound of claim 1 which is N,N'-Bis[3-(10,11-dihydro-5H-dibenzo[b,f]azepino)propyl]-N,N'-dimethylpentanediamine Maleate.

12. A compound of claim 1 which is N,N'-Bis[3-(10,11-dihydro-5H-dibenzo[b,f]azepino)propyl]-N,N'-dimethylhexanediamine Fumarate.

13. A compound of claim 1 which is N,N'-Bis[3-(10,11-dihydro-5H-dibenzo[b,f]azepino)propyl]-N,N'-dibenzylbutanediamine.

14. A compound of claim 1 which is N,N'-Bis[3-(10,11-dihydro-5H-dibenzo[b,f]azepino)-propyl]-butanediamine Maleate.

15. A compound of claim 1 which is 1,4-Bis[3-(10,11-dihydro-5H-dibenzo[b,f]azepino)propyl]piperazine Maleate.

* * * * *